United States Patent
Tang et al.

(10) Patent No.: US 10,538,506 B2
(45) Date of Patent: Jan. 21, 2020

(54) CRYSTAL FORM OF A POTASSIUM-COMPETITIVE ACID BLOCKER AND PREPARATION METHOD THEREOF

(71) Applicant: Jiangsu Hansoh Pharmaceutical Group Co., Ltd., Lianyungang, Jiangsu (CN)

(72) Inventors: Hongwei Tang, Lianyungang (CN); Changan Sun, Lianyungang (CN); Ruijun Wang, Lianyungang (CN); Hengli Yuan, Lianyungang (CN)

(73) Assignee: Jiangsu Hansoh Pharmaceutical Group Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/524,694

(22) PCT Filed: Nov. 9, 2015

(86) PCT No.: PCT/CN2015/094120
§ 371 (c)(1),
(2) Date: May 5, 2017

(87) PCT Pub. No.: WO2016/074597
PCT Pub. Date: May 19, 2016

(65) Prior Publication Data
US 2018/0282300 A1    Oct. 4, 2018

(30) Foreign Application Priority Data
Nov. 12, 2014 (CN) .......................... 2014 1 0637759

(51) Int. Cl.
*C07D 401/12*   (2006.01)
(52) U.S. Cl.
CPC ........ *C07D 401/12* (2013.01); *C07B 2200/13* (2013.01)
(58) Field of Classification Search
CPC ................................... C07D 401/12
USPC ....................... 546/278.4; 514/343
See application file for complete search history.

(56) References Cited

U.S. PATENT DOCUMENTS 6,627,646 B2 *  9/2003  Bakale .............. C07D 401/12
                                                514/303

FOREIGN PATENT DOCUMENTS

| CN | 101300229 | A | 11/2008 |
| CN | 104327051 | * | 2/2015 |

OTHER PUBLICATIONS

Guillory (in Brittain ed.), "Polymorphism in Pharmaceutical Solids" NY:Marcel Dekker, Inc. 1-2, 183-226. (Year: 1999).*
CMU Pharmaceutical polymorphism, Internet p. 1-3 Apr. 3, 2008. (Year: 2002).*
Singhal et al., "Drug Polymorphism, etc.," Advanced Drug Reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffer et al., "Polymorphism and Drug Availabity, etc.," J of Pharm. (Lahore), 1(1), 59-66. (Year: 1979).*
U.S. Pharmacopia #23, National Formulary #18, 1843-1844. (Year: 1995).*
Doelker, english translation of S.T.P. Pratiques, 9(5), 399-409, pp. 1-33. (Year: 1999).*
Doelker, english translation of Ann. Pharm. Fr., 60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull. 47(6) 852-856. (Year: 1999).*
Int'l Search Report dated Feb. 3, 2016 in Int'l Application No. PCT/CN2015/094120.

* cited by examiner

*Primary Examiner* — Patricia L Morris
(74) *Attorney, Agent, or Firm* — Panitch Schwarze Belisario & Nadel LLP

(57) ABSTRACT

The present invention relates to a crystal form of a potassium-competitive acid blocker, that is, 1-[5-(2-fluorophenyl)-1-(pyridine-3-sulfonyl)-1H-pyrrole-3-yl]-N-methyl methylamine fumaric acid salt (which is briefly referred to as a formula I) and a preparation method thereof. An X-ray powder diffraction characteristic peak thereof is shown in FIG. 1. The crystal form that is represented by formula I, provided in the present invention, is stable, reproducible, and is suitable for drug development.

Formula I

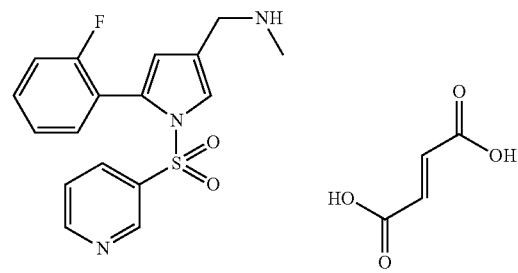

5 Claims, 2 Drawing Sheets

CRYSTAL FORM OF A POTASSIUM-COMPETITIVE ACID BLOCKER AND PREPARATION METHOD THEREOF

CROSS-REFERENCE TO RELATED APPLICATION

This application is a Section 371 of International Application No. PCT/CN2015/094120, filed Nov. 9, 2015, which was published in the Chinese language on May 19, 2016, under International Publication No. WO 2016/074597 A1, and the disclosure of which is incorporated herein by reference.

FIELD OF THE INVENTION

The present invention relates to the field of medicinal chemistry, and specifically relates to a crystal form of a potassium-competitive acid blocker, namely 1-[5-(2-fluorophenyl)-1-(pyridin-3-ylsulfonyl)-1H-pyrrol-3-yl]-N-methylmethanamine fumarate, and a preparation method thereof.

BACKGROUND OF THE INVENTION

1-[5-(2-fluorophenyl)-1-(pyridin-3-ylsulfonyl)-1H-pyrrol-3-yl]-N-methylmethanamine fumarate was developed by Takeda Pharmaceutical company, for use in treating an acid-related disease (e.g., duodenal ulcer, esophagitis, gastroesophageal reflux disease, eradicating *Helicobacter pylori*, peptic ulcer, gastric ulcer). 1-[5-(2-fluorophenyl)-1-(pyridin-3-ylsulfonyl)-1H-pyrrol-3-yl]-N-methylmethanamine fumarate is a potassium-competitive acid blocker (P-CAB), which functions by competitively inhibiting potassium ions in the hydrogen ion/potassium ion-ATP enzyme. It is a reversible potassium antagonist, and belongs to a novel proton pump inhibitor. Its structural formula is as follows:

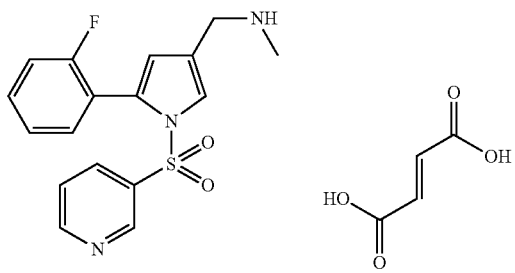 [SMILES: CNCc1cc(-c2ccccc2F)n(S(=O)(=O)c2cccnc2)c1 ; O=C(O)/C=C/C(=O)O]

There are currently no reports of crystal forms of 1-[5-(2-fluorophenyl)-1-(pyridin-3-ylsulfonyl)-1H-pyrrol-3-yl]-N-methylmethanamine fumarate and preparation methods thereof.

SUMMARY OF THE INVENTION

An objective of the present invention is to provide a novel crystal form of 1-[5-(2-fluorophenyl)-1-(pyridin-3-ylsulfonyl)-1H-pyrrol-3-yl]-N-methylmethanamine fumarate of formula I.

The crystal form can be identified by its characteristic X-ray powder diffraction (XRPD) spectrum.

The crystal form can be characterized by a characteristic X-ray powder diffraction (XRPD) spectrum, which comprises peaks at $2\theta \pm 0.2°$: 12.30, 13.59, 15.34, 18.67, 20.48, 21.69, 25.23, 26.92°, wherein the X-ray powder diffraction spectrum is obtained by using $CuK_{\alpha 1}$ radiation.

Particularly preferably, the characteristic XRPD peaks of the crystal form of the potassium-competitive acid blocker of the present invention are shown in the table below:

| $2\theta$ (°) |
| --- |
| 5.24 |
| 11.51 |
| 11.76 |
| 12.30 |
| 13.59 |
| 14.02 |
| 15.34 |
| 16.22 |
| 16.96 |
| 17.48 |
| 17.92 |
| 18.67 |
| 19.20 |
| 20.48 |
| 20.85 |
| 21.69 |
| 22.53 |
| 23.10 |
| 23.59 |
| 24.50 |
| 25.23 |
| 25.65 |
| 26.21 |
| 26.92 |
| 27.80 |
| 28.91 |
| 30.46 |
| 30.68 |
| 32.83 |
| 33.92 |
| 34.92 |
| 36.21 |

Further preferably, the XRPD data of the crystal form is shown as follows:

TABLE 1

X-ray powder diffraction data of the crystal form of the compound of formula I:

| $2\theta$ (°) | d-value (Å) | Intensity $I/I_0$ (%) |
| --- | --- | --- |
| 5.24 | 16.847 | 7.3 |
| 11.51 | 7.684 | 34.3 |
| 11.76 | 7.521 | 39.5 |
| 12.30 | 7.188 | 70.1 |
| 13.59 | 6.512 | 100 |
| 14.02 | 6.312 | 19.1 |
| 15.34 | 5.770 | 96.5 |
| 16.22 | 5.460 | 13.7 |
| 16.96 | 5.224 | 37.0 |
| 17.48 | 5.069 | 45.5 |
| 17.92 | 4.945 | 17.7 |
| 18.67 | 4.749 | 88.9 |
| 19.20 | 4.620 | 9.4 |
| 20.48 | 4.333 | 92.4 |
| 20.85 | 4.256 | 36.7 |
| 21.69 | 4.094 | 69.4 |
| 22.53 | 3.943 | 24.3 |
| 23.10 | 3.847 | 31.0 |
| 23.59 | 3.768 | 6.2 |
| 24.50 | 3.630 | 12.4 |
| 25.23 | 3.528 | 96.7 |
| 25.65 | 3.471 | 34.7 |
| 26.21 | 3.398 | 13.6 |
| 26.92 | 3.310 | 76.0 |
| 27.80 | 3.207 | 30.4 |
| 28.91 | 3.086 | 5.3 |

TABLE 1-continued

X-ray powder diffraction data of the crystal form of the compound of formula I:

| 2θ (°) | d-value (Å) | Intensity I/I₀ (%) |
|---|---|---|
| 30.46 | 2.932 | 12.4 |
| 30.68 | 2.912 | 18.8 |
| 32.83 | 2.726 | 7.6 |
| 33.92 | 2.640 | 10.5 |
| 34.92 | 2.567 | 15.2 |
| 36.21 | 2.479 | 9.7 |

Moreover, the crystal form of the compound of formula I can be characterized by a melting point of about 206° C.±3° C. (determined by DSC; evaluated by the starting temperature; with a heating rate of 10 K/minute). The DSC curve obtained is shown in FIG. 2.

In order to allow experimental error, the aforementioned 2θ should be considered to be accurate to 2θ±0.20. In other words, when determining whether or not a crystal sample of a given compound A is the crystal form of the present invention, if the 2θ value of the sample observed in an experiment falls into the ±0.2° range of a 2θ characteristic value, then it should be considered to be the same as the aforementioned characteristic value.

In another aspect, the present invention relates to a method of preparing the crystal form of formula I, comprising the following steps of:

(a) dissolving 1-[5-(2-fluorophenyl)-1-(pyridin-3-ylsulfonyl)-1H-pyrrol-3-yl]-N-methylmethanamine fumarate in a solvent or a mixture of solvents to form a saturated or nearly saturated solution;

(b) storing the solution in order to precipitate the crystal form from the solution, thereby forming a suspension;

(c) separating the precipitate from the suspension; and (d) drying the precipitate to remove the solvent or the mixture of solvents.

Preferably, the solvent is selected from the group consisting of $C_{1-4}$-alkanol, water, ethyl acetate, acetonitrile, acetone, methyl tert-butyl ether, N,N-dimethyl formamide, and a mixture of two or more of these solvents.

Preferably, step (a) is carried out at room temperature (about 20° C.) or at a rising temperature about below the boiling point of the solvent used or the mixture of solvents used.

Optionally, one or more poor solvents can be added in step (a) and/or step (b) to reduce the solubility of formula I in the solution.

Preferably, the temperature of the solution in step (b) can be room temperature (about 20° C.) or below.

Optionally, step (b) can be carried out with or without stirring.

Optionally, a seed crystal can be added or not added in step (b).

Preferably, in step (c), the precipitate can be separated by means using known methods, such as filtration, suction filtration, spin filtration, decantation or centrifugation.

Preferably, in step (d), the filtered solvent or the mixture of solvents can be removed under conditions of normal pressure or reduced pressure, heating or no heating.

Another objective of present invention is to provide a pharmaceutical composition comprising the crystal form.

The crystal form of the compound of formula I provided by the present invention is stable, reproducible, and suitable for drug development.

DETAILED DESCRIPTION OF THE INVENTION

In order to further illustrate the present invention, the present invention will be described in detail with reference to the specific examples below, but the scope of the present invention is not limited to these specific examples.

EXAMPLE 1

Figure 1:
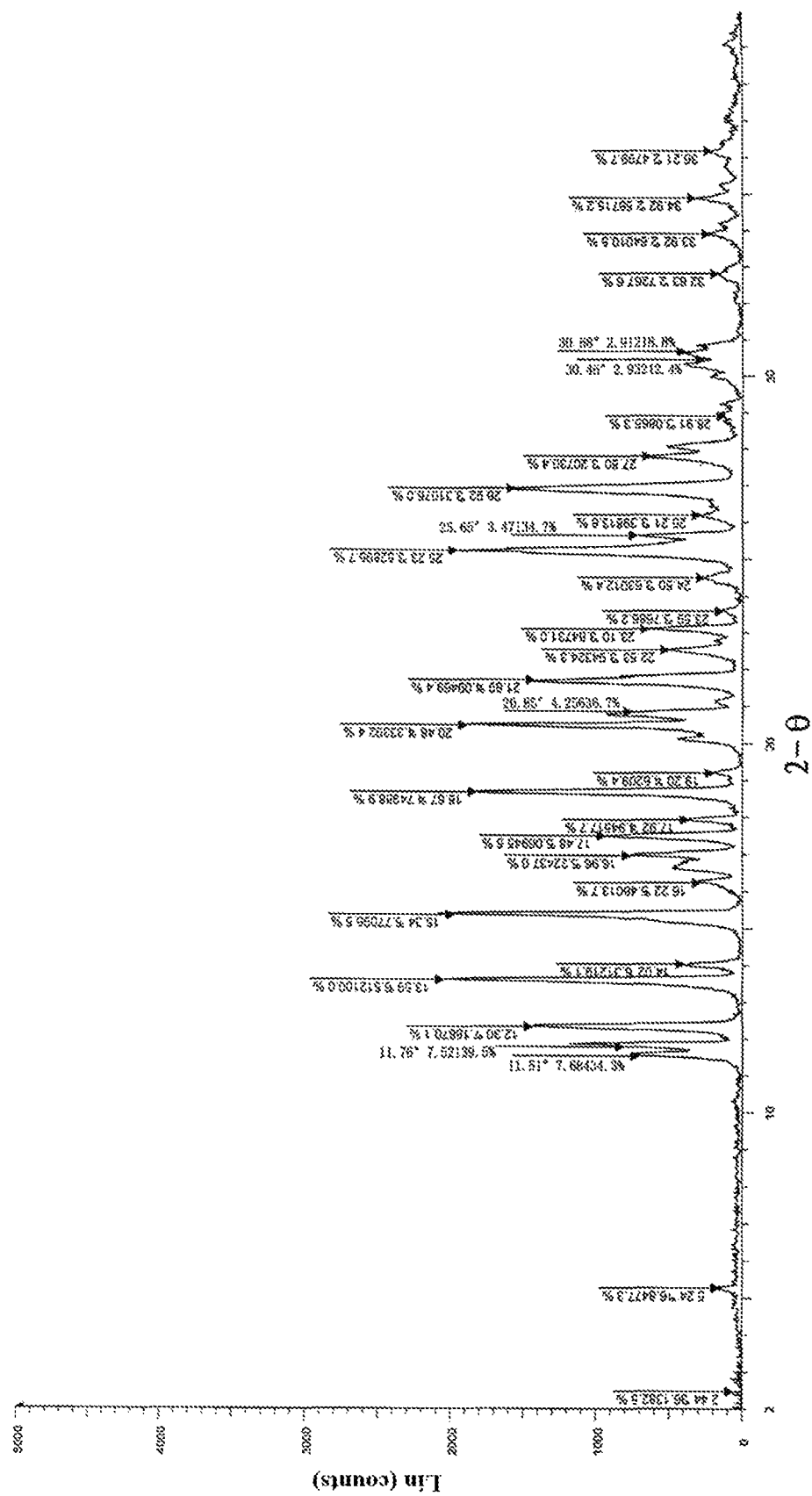
FIG. 1 shows the X-ray powder diffraction spectrum of the crystal form of the compound of formula I of the present invention.
Figure 2:
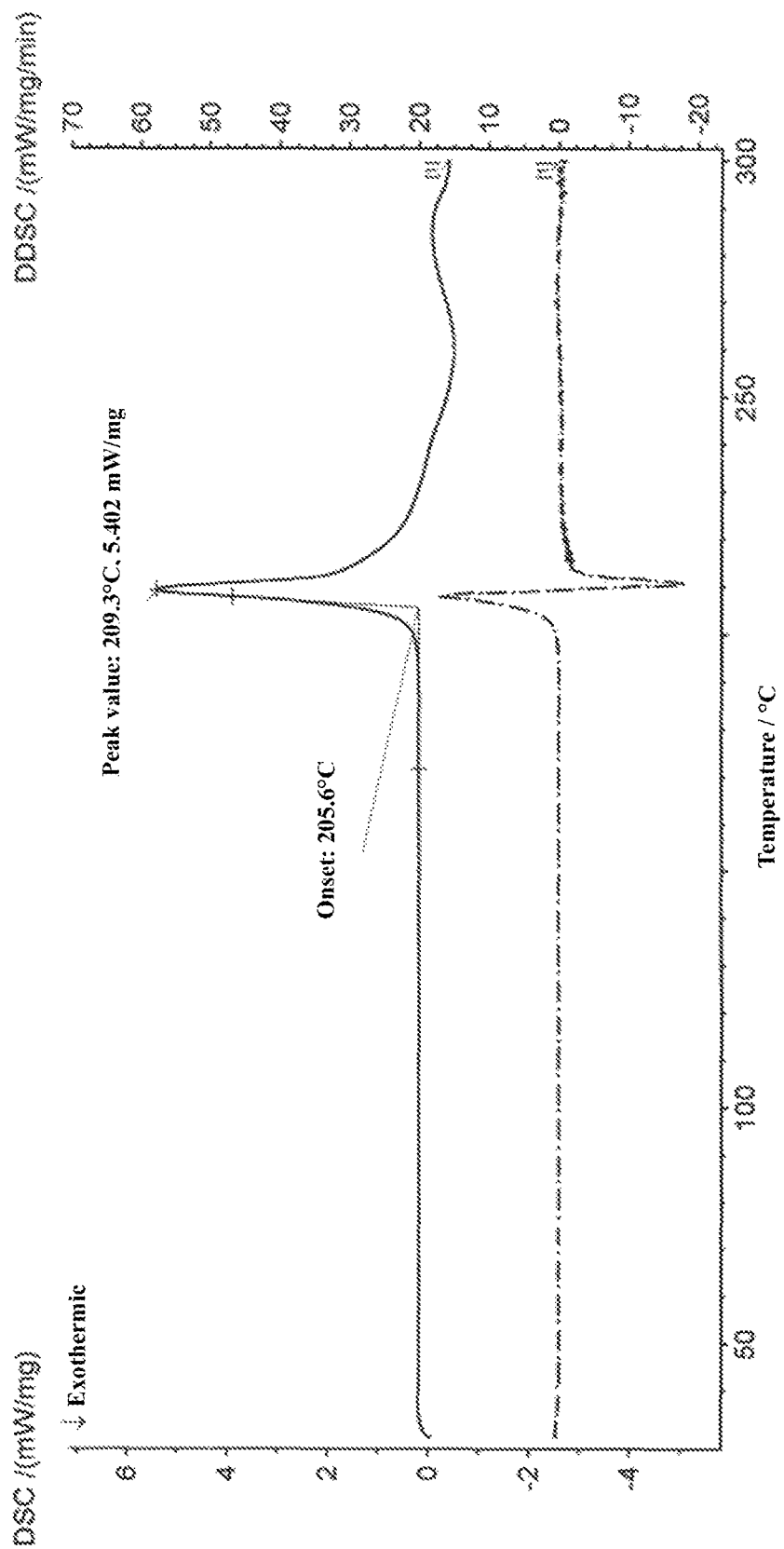
FIG. 2 shows the DSC spectrum of the crystal form of the compound of formula I.

2 g of 1-[5-(2-fluorophenyl)-1-(pyridin-3-ylsulfonyl)-1H-pyrrol-3-yl]-N-methylmethanamine fumarate were dissolved in 20 ml of a mixture of water/isopropanol (volume ratio 3:7), which had been heated to about 70° C. The solution was cooled to about 5° C. in 3 to 5 hours, stirred for 1 hour, and filtered under reduced pressure. The filter cake was dried at 50° C. for 8 hours to obtain 1.4 g of a crystal form. The XRPD spectrum and DSC spectrum of the crystal form are shown in FIGS. 1 and 2, respectively.

EXAMPLE 2

2 g of 1-[5-(2-fluorophenyl)-1-(pyridin-3-ylsulfonyl)-1H-pyrrol-3-yl]-N-methylmethanamine fumarate were dissolved in 80 ml of a mixture of ethyl acetate/methanol (volume ratio 1:7), which had been heated to about 70° C. The solution was cooled to about 5° C. in 3 to 5 hours, stirred for 1 hour, and filtered under reduced pressure. The filter cake was dried at 50° C. for 8 hours to obtain 1.2 g of a crystal form. The XRPD spectrum of the crystal form was substantially consistent with FIG. 1, and the DSC spectrum of the crystal form is shown in FIG. 2.

EXAMPLE 3

2 g of 1-[5-(2-fluorophenyl)-1-(pyridin-3-ylsulfonyl)-1H-pyrrol-3-yl]-N-methylmethanamine fumarate were dissolved in 80 ml of methanol, which had been heated to about 65° C. The solution was cooled to about 5° C. in 3 to 5 hours, stirred for 1 hour, and filtered under reduced pressure. The filter cake was dried at 50° C. for 8 hours to obtain 1.0 g of a crystal form. The XRPD spectrum of the crystal form was substantially consistent with FIG. 1, and the DSC spectrum of the crystal form is shown in FIG. 2.

EXAMPLE 4

2 g of 1-[5-(2-fluorophenyl)-1-(pyridin-3-ylsulfonyl)-1H-pyrrol-3-yl]-N-methylmethanamine fumarate were dissolved in 30 ml of water, which had been heated to about 95° C. The solution was cooled to about 5° C. in 3 to 5 hours, stirred for 1 hour, and filtered under reduced pressure. The filter cake was dried at 50° C. for 8 hours to obtain 1.5 g of a crystal form. The XRPD spectrum of the crystal form was substantially consistent with FIG. 1, and the DSC spectrum of the crystal form is shown in FIG. 2.

Experimental Example 1: Comparative Study on the Crystal Forms of Samples Before and after Stability Testing The samples were prepared according to the method of Example 1, then were placed under the long-term stability conditions (temperature: 30° C.; humidity: 65%) for six months. The X-ray powder diffractions of the samples were then determined. The X-ray powder diffraction spectra were analyzed, and compared with the starting data. The comparison data are shown in Table 2:

TABLE 2

Comparison of the X-ray powder diffraction data of the samples placed under long-term stability conditions

| Numbers | At the beginning | | For six months under long-term stability conditions | |
|---|---|---|---|---|
| | 2θ (°) | d-value (Å) | 2θ (°) | d-value (Å) |
| 1 | 11.51 | 7.684 | 11.53 | 7.671 |
| 2 | 11.76 | 7.521 | 11.78 | 7.508 |
| 3 | 12.30 | 7.188 | 12.32 | 7.180 |
| 4 | 13.59 | 6.512 | 13.61 | 6.503 |
| 5 | 14.02 | 6.312 | 14.04 | 6.304 |
| 6 | 15.34 | 5.770 | 15.36 | 5.765 |
| 7 | 16.22 | 5.460 | 16.24 | 5.455 |
| 8 | 16.96 | 5.224 | 16.98 | 5.219 |
| 9 | 17.48 | 5.069 | 17.50 | 5.065 |
| 10 | 17.92 | 4.945 | 17.95 | 4.939 |
| 11 | 18.67 | 4.749 | 18.69 | 4.745 |
| 12 | 20.48 | 4.333 | 20.51 | 4.328 |
| 13 | 20.85 | 4.256 | 20.87 | 4.254 |
| 14 | 21.69 | 4.094 | 21.71 | 4.091 |
| 15 | 22.53 | 3.943 | 22.55 | 3.941 |
| 16 | 23.10 | 3.847 | 23.12 | 3.845 |
| 17 | 24.50 | 3.630 | 24.52 | 3.628 |
| 18 | 25.23 | 3.528 | 25.25 | 3.525 |
| 19 | 25.65 | 3.471 | 25.67 | 3.468 |
| 20 | 26.21 | 3.398 | 26.23 | 3.396 |
| 21 | 26.92 | 3.310 | 26.94 | 3.308 |
| 22 | 27.80 | 3.207 | 27.82 | 3.205 |
| 23 | 30.46 | 2.932 | 30.48 | 2.931 |
| 24 | 30.68 | 2.912 | 30.70 | 2.910 |
| 25 | 33.92 | 2.640 | 33.94 | 2.639 |
| 26 | 34.92 | 2.567 | 34.94 | 2.567 |

Conclusion: After comparing the aforementioned XRPD spectra, it was found that there were no obvious changes in d-values and 2θ angles of the diffraction peaks. After being placed under long-term stability conditions (temperature: 30° C.; humidity: 65%) for six months, the crystal forms of three batches of samples had not changed.

Experimental Example 2: Comparative Study on the Crystal Forms Before and after Grinding The samples were prepared according to the method of Example 1, and the following tests were carried out:

(1) directly grinding the sample for 5 minutes; and (2) directly micronizing the samples.

The X-ray powder diffraction test was carried out on the aforementioned two samples respectively, and the data was compared with the starting data. The comparison data are shown in Table 3.

TABLE 3

Comparison of the X-ray powder diffraction data of the samples before and after grinding and micronization

| Numbers | At the beginning | | Data obtained after grinding | | Data obtained after micronization | |
|---|---|---|---|---|---|---|
| | 2θ (°) | d-value (Å) | 2θ (°) | d-value (Å) | 2θ (°) | d-value (Å) |
| 1 | 11.51 | 7.684 | 11.50 | 7.691 | 11.54 | 7.664 |
| 2 | 11.76 | 7.521 | 11.75 | 7.527 | 11.79 | 7.502 |
| 3 | 12.30 | 7.188 | 12.29 | 7.198 | 12.33 | 7.175 |
| 4 | 13.59 | 6.512 | 13.58 | 6.517 | 13.62 | 6.498 |
| 5 | 14.02 | 6.312 | 14.01 | 6.318 | 14.05 | 6.300 |
| 6 | 15.34 | 5.770 | 15.33 | 5.777 | 15.37 | 5.762 |
| 7 | 16.22 | 5.460 | 16.21 | 5.465 | 16.25 | 5.452 |
| 8 | 16.96 | 5.224 | 16.95 | 5.228 | 16.99 | 5.216 |
| 9 | 17.48 | 5.069 | 17.47 | 5.074 | 17.51 | 5.062 |
| 10 | 17.92 | 4.945 | 17.91 | 4.950 | 17.95 | 4.939 |
| 11 | 18.67 | 4.749 | 18.66 | 4.753 | 18.70 | 4.743 |
| 12 | 20.48 | 4.333 | 20.47 | 4.336 | 20.51 | 4.328 |
| 13 | 20.85 | 4.256 | 20.84 | 4.260 | 20.88 | 4.252 |
| 14 | 21.69 | 4.094 | 21.68 | 4.097 | 21.72 | 4.090 |
| 15 | 22.53 | 3.943 | 22.52 | 3.946 | 22.56 | 3.939 |
| 16 | 23.10 | 3.847 | 23.09 | 3.850 | 23.13 | 3.843 |
| 17 | 24.50 | 3.630 | 24.49 | 3.633 | 24.53 | 3.627 |
| 18 | 25.23 | 3.528 | 25.22 | 3.529 | 25.26 | 3.523 |
| 19 | 25.65 | 3.471 | 25.64 | 3.472 | 25.68 | 3.467 |
| 20 | 26.21 | 3.398 | 26.20 | 3.399 | 26.24 | 3.394 |
| 21 | 26.92 | 3.310 | 26.91 | 3.311 | 26.95 | 3.307 |
| 22 | 27.80 | 3.207 | 27.79 | 3.209 | 27.83 | 3.204 |
| 23 | 30.46 | 2.932 | 30.45 | 2.934 | 30.49 | 2.930 |
| 24 | 30.68 | 2.912 | 30.67 | 2.913 | 30.71 | 2.910 |
| 25 | 33.92 | 2.640 | 33.91 | 2.642 | 33.95 | 2.639 |
| 26 | 34.92 | 2.567 | 34.91 | 2.569 | 34.95 | 2.566 |

Conclusion: The crystal forms of the samples had not changed under the conditions of direct grinding and micronization.

Experimental Example 3: Study on Hygroscopicity of Samples

The samples were prepared according to the method of Example 1, and the following tests were carried out:

(1) placing the sample at 25° C. and 75% humidity;

(2) placing the sample at 25° C. and 92.5% humidity.

The aforementioned two samples were taken and tested at different time points to investigate weight gain of the samples due to moisture absorption. The comparison data are shown in Table 4.

TABLE 4

Comparison of weight gain of the samples due to moisture absorption

| Items investigated | High humidity test 25° C./ RH 75% (days) | | | | High humidity test 25° C./ RH 92.5% (days) | | | |
|---|---|---|---|---|---|---|---|---|
| | 0 | 5 | 10 | 30 | 0 | 5 | 10 | 30 |
| weight gain due to moisture absorption (%) | — | 0.01 | 0.13 | 0.12 | — | 0.17 | 0.12 | 0.19 |

Conclusion: The samples did not show hygroscopicity.

Experimental Example 4: Comparative Study on Samples Before and after Stability Testing The samples were prepared according to the method of Example 1, and then were placed under the long-term stability conditions (temperature: 30° C.±2° C.; humidity: 65%±5%) for six months. The inspection items were tested, and the comparison data are shown in Table 5:

TABLE 5

Comparison of the data of samples placed under long-term stability conditions

| | Time (months) | | |
|---|---|---|---|
| Inspection items | 0 | 3 | 6 |
| Appearance | White powder | White powder | White powder |
| HPLC identification | Consistent | Consistent | Consistent |
| Clarity and color of dimethylsulfoxide solution | Clear and colorless | Clear and colorless | Clear and colorless |
| Related substance (%) Maximum unknown single impurity | 0.03 | 0.04 | 0.03 |
| Total impurities | 0.12 | 0.13 | 0.13 |
| Moisture (%) | 0.04 | 0.08 | 0.08 |
| Particle size | d (0.5) ≤15 μm d (0.9) ≤30 μm | d (0.5) ≤15 μm d (0.9) ≤30 μm | d (0.5) ≤15 μm d (0.9) ≤30 μm |
| Content (%) | 99.6 | 100.0 | 99.7 |

Conclusion: The samples had good stability under the long-term storage conditions.

Experimental Example 5: Study on Dissolution of Tablets Prepared from Samples

Active pharmaceutical ingredient (API) tablets (conventional tabletting) were obtained from the samples prepared according to the method of Example 1. The dissolution rates of the samples were investigated in 0.1 mol/L HCl solution, acetate buffer pH 4.5, phosphate buffer pH 6.8 and purified water, respectively. The comparison data are shown in Table 6:

TABLE 6

Dissolution data of 20 mg specification products (n = 6)

| | Medium | | | | | | | |
|---|---|---|---|---|---|---|---|---|
| | 0.1 mol/L HCl | | Purified water | | Acetate buffer pH 4.5 | | Phosphate buffer pH 6.8 | |
| Time (min) | X (%) | RSD (%) | X (%) | RSD (%) | X (%) | RSD (%) | X (%) | RSD (%) |
| 10 | 94 | 2.8 | 92 | 3.4 | 93 | 3.4 | 90 | 1.7 |
| 15 | 97 | 2.4 | 95 | 3.7 | 97 | 2.4 | 94 | 1.8 |
| 30 | 99 | 1.1 | 95 | 2.3 | 99 | 3.2 | 95 | 1.4 |
| 45 | 101 | 1.2 | 98 | 2.1 | 101 | 3.7 | 99 | 1.0 |

Conclusion: The dissolution results of the tablets prepared from the samples showed that the dissolution rates of the tabletsin 0.1 mol/L HCl solution, acetate buffer pH 4.5, phosphate buffer pH 6.8 and purified water were all more than 85% at 15 minutes.

It can be seen from the stability inspection data of the samples that the crystal form of the present invention has good stability, and conforms to medicinal quality standards.

We claim:

1. A crystal form of 1-[5-(2-fluorophenyl)-1-(pyridin-3-ylsulfonyl)-1H-pyrrol-3-yl]-N-methylmethanamine fumarate, wherein the crystal has a characteristic X-ray powder diffraction spectrum comprising diffraction peaks at diffraction angles (2θ±0.2°): 12.30, 13.59, 15.34, 18.67, 20.48, 21.69, 25.23, and 26.92.

2. The crystal form according to claim 1, wherein the characteristic X-ray powder diffraction spectrum further comprises diffraction peaks at diffraction angles (2θ±0.2°):

| 2θ (°) |
|---|
| 5.24 |
| 11.51 |
| 11.76 |
| 14.02 |
| 16.22 |
| 16.96 |
| 17.48 |
| 17.92 |
| 19.20 |
| 20.85 |
| 22.53 |
| 23.10 |
| 23.59 |
| 24.50 |
| 25.65 |
| 26.21 |
| 27.80 |
| 28.91 |
| 30.46 |
| 30.68 |
| 32.83 |
| 33.92 |
| 34.92 |
| 36.21. |

3. The crystal form according to claim 1, wherein the crystal form has the following d-values at the indicated diffraction angles (2θ±0.2°):

| 2θ (°) | d-value (Å) |
|---|---|
| 5.24 | 16.847 |
| 11.51 | 7.684 |
| 11.76 | 7.521 |
| 12.30 | 7.188 |
| 13.59 | 6.512 |
| 14.02 | 6.312 |
| 15.34 | 5.770 |
| 16.22 | 5.460 |
| 16.96 | 5.224 |
| 17.48 | 5.069 |
| 17.92 | 4.945 |
| 18.67 | 4.749 |
| 19.20 | 4.620 |
| 20.48 | 4.333 |
| 20.85 | 4.256 |
| 21.69 | 4.094 |
| 22.53 | 3.943 |
| 23.10 | 3.847 |
| 23.59 | 3.768 |
| 24.50 | 3.630 |
| 25.23 | 3.528 |
| 25.65 | 3.471 |
| 26.21 | 3.398 |
| 26.92 | 3.310 |
| 27.80 | 3.207 |
| 28.91 | 3.086 |
| 30.46 | 2.932 |
| 30.68 | 2.912 |
| 32.83 | 2.726 |
| 33.92 | 2.640 |
| 34.92 | 2.567 |
| 36.21 | 2.479. |

4. The crystal form according to claim 1, wherein a melting point of the crystal form is 206° C.±3° C.

5. A crystal form of 1-[5-(2-fluorophenyl)-1-(pyridin-3-ylsulfonyl)-1H-pyrrol-3-yl]-N-methylmethanamine fumarate, wherein the crystal has an X-ray powder diffraction spectrum as shown in FIG. 1.

* * * * *